United States Patent

Dekeyser et al.

Patent Number: 5,567,723
Date of Patent: Oct. 22, 1996

[54] MITICIDAL HYDRAZINE COMPOUNDS AND THEIR INTERMEDIATES

[75] Inventors: Mark A. Dekeyser, Waterloo; Derek J. McPhee, Guelph, both of Canada; Paul T. McDonald, Middlebury, Conn.

[73] Assignees: Uniroyal Chemical Company, Inc., Middlebury, Conn.; Uniroyal Chemical Ltd./Ltee, Elmira, Canada

[21] Appl. No.: 498,102

[22] Filed: Jul. 5, 1995

[51] Int. Cl.$^6$ .................. C07D 213/02; A01N 43/40; A01N 33/26; C07C 243/24

[52] U.S. Cl. .................. 514/357; 514/345; 514/352; 514/365; 514/369; 514/370; 514/438; 514/445; 514/447; 514/614; 514/656; 546/300; 546/306; 546/309; 546/332; 546/335; 548/187; 548/194; 548/198; 548/204; 549/65; 549/68; 549/77; 564/148; 564/151

[58] Field of Search .................. 514/345, 352, 514/357, 365, 369, 370, 438, 445, 447, 614, 656; 546/300, 306, 309, 332, 335; 548/187, 194, 198, 204; 549/65, 68, 77; 564/151, 148

[56] References Cited

U.S. PATENT DOCUMENTS

| | | | |
|---|---|---|---|
| 2,547,724 | 4/1951 | Sundholm | 549/23 |
| 4,725,302 | 2/1988 | Ehrenfreund | 71/88 |
| 5,367,093 | 11/1994 | Dekeyser | 560/27 |

FOREIGN PATENT DOCUMENTS

| | | |
|---|---|---|
| 0067471 | 12/1982 | European Pat. Off. . |
| 0183650 | 6/1986 | European Pat. Off. . |

OTHER PUBLICATIONS

Beilstein, RN 20943-67-3, referenced by Hunisch et al, Arzneim. Forsch, vol. 18, 1968, pp. 1324–1325.
Chemical Abstracts 108: 163280d, vol. 108, No. 19, May 9, 1988.
Chemical Abstracts 105: 152687d, vol. 105, No. 17, Oct. 27, 1986.

*Primary Examiner*—Zinna Northington Davis
*Attorney, Agent, or Firm*—Daniel Reitenbach

[57] ABSTRACT

Compounds having the structural formula

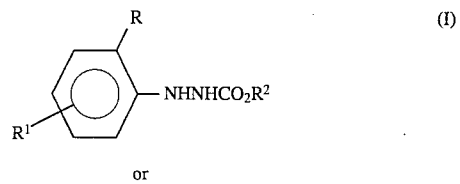

or

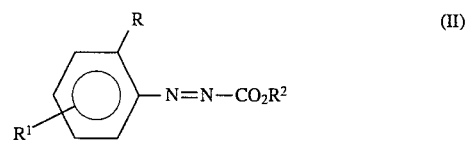

wherein R is $C_1$–$C_6$ alkoxy or $C_1$–$C_6$ alkyl; $R^1$ is fluorenyl, thienyl, pyridyl or thiazolyl, unsubstituted or substituted by one or more substituents selected from $C_1$–$C_4$ alkoxy, $C_1$–$C_4$ alkyl, $C_1$–$C_4$ alkylthio, halogen, $C_1$–$C_4$ haloalkyl and nitro; and $R^2$ is $C_1$–$C_6$ alkyl, $C_3$–$C_6$ cycloalkyl, $C_1$–$C_6$ haloalkyl, $C_2$–$C_6$ alkenyl, or $C_2$–$C_6$ alkoxyalkyl. The compounds of this invention are effective for controlling mites and nematodes.

20 Claims, No Drawings

MITICIDAL HYDRAZINE COMPOUNDS AND THEIR INTERMEDIATES

FIELD OF THE INVENTION

This invention is directed to novel hydrazine derivatives which exhibit activity as miticides and nematicides. This invention is also directed to miticidal and nematicidal compositions comprising such hydrazine derivatives.

BACKGROUND OF THE INVENTION

Destruction of crops by nematodes and mites presents a serious problem to agriculture. A wide variety of field crops are in need of protection from nematodes and mites including such valuable crops as soybeans, corn, peanuts, cotton, alfalfa and tobacco. In addition, vegetables, such as tomatoes, potatoes, sugarbeet, carrots and the like as well as fruits, nuts, ornamentals and seed bed crops such as apples, peaches, pears, citrus fruit and grapes may also require protection from the ravages of such pests. Particularly difficult types of insects to control are those which, at one or more stages of their life, inhabit the soil and cause destruction to the roots of agriculturally valuable plants. For this reason the development of new, more effective nematocides represents an ongoing scientific activity. More particularly, the development of acaricides which are effective as both ovicides and larvicides are of interest.

Chemical Abstracts 108(19):163280d describes certain alkyl phenylhydrazinecarboxylates and the preparation and acaricidal use thereof. U.S. Pat. No. 4,725,302 describes certain substituted phenylhydrazines and phenyloxadiazolinones and pesticidal uses thereof. European Patent 067 471 describes certain 7-substituted 2,3-dihydrobenzofurans, their preparation, and their use as pesticides or chemical intermediates. DerWent Abstract 88-312695/44 describes certain arylhydrazides of trifluoroacetic acid that have fungicidal, bacteriocidal, acaricidal, and antiseptic activity. U.S. Pat. No. 5,367,093 describes certain insecticidal phenylhydrazine derivatives.

It is the purpose of this to provide novel hydrazine derivatives useful as miticides and nemotacides.

SUMMARY OF THE INVENTION

The present invention relates to a compound having the formula:

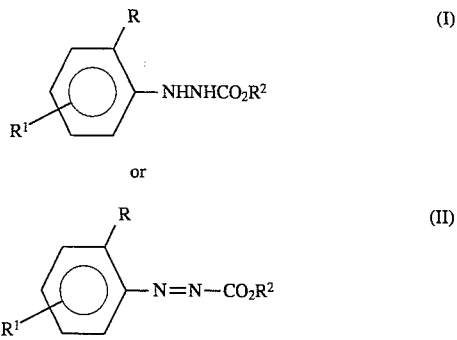

wherein R is $C_1$–$C_6$ alkoxy or $C_1$–$C_6$ alkyl; $R^m$ is fluorenyl, thienyl, pyridyl or thiazolyl, unsubstituted or substituted by one or more substituents selected from $C_1$–$C_4$ alkoxy, $C_1$–$C_4$ alkyl, $C_1$–$C_4$ alkylthio, halogen, $C_1$–$C_4$ haloalkyl and nitro; and $R^2$ is $C_1$–$C_6$ alkyl, $C_3$–$C_6$ cycloalkyl, $C_1$–$C_6$ haloalkyl, $C_2$–$C_6$ alkenyl, or $C_2$–$C_6$ alkoxyalkyl.

Compounds of formula (I) and (II), and compositions comprising the compounds, are useful as miticides and nematocides.

DETAILED DESCRIPTION OF THE INVENTION

Preferred compounds of formula (I) and (II) are those compounds wherein R is $C_1$–$C_4$ alkoxy or $C_1$–$C_4$ alkyl; $R^1$ is fluorenyl, thienyl, pyridyl or thiazolyl, unsubstituted or substituted by one or more $C_1$–$C_4$ alkyl; and $R^2$ is $C_1$–$C_4$ alkyl. More preferred compounds of formula (I) and (II) are those compounds in which R is methoxy or methyl; $R^1$ is 2-methyl-4-thiazolyl, 2-pyridinyl, 2-thienyl, 3-pyridinyl, or 9H-fluoren-3-yl; and $R^2$ is 1-methylethyl.

The compounds of the instant invention may be prepared by reacting an intermediate hydrazine derivative of the formula

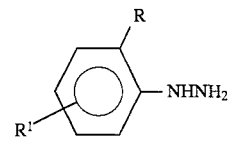

wherein R and R' are as described above, with an acyl halide of the formula $ClCO_2R^2$, wherein $R^2$ is as described above.

The intermediate hydrazine derivative can be prepared by diazetizing the corresponding aniline with sodium nitrite followed by reduction with stannous chloride.

The pesticidal compositions of this invention comprise (a) a compound having a structure within that of formula (I) or (II) above and (b) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water. Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/ formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To combat pests, sprays of the compounds may be applied to the pests directly and/or to plants upon which they feed or nest. The pesticidally active formulations may also be applied to the soil or other medium in which the pests are present.

Harmful nematodes and mites attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as nematocides and miticides, for foliar and/or soil application.

The following examples are presented to further illustrate the present invention.

EXAMPLE 1

Preparation of 1-methylethyl 2-[2-methoxy-5-(2-methyl-4-thiazolyl)phenyl]hydrazinecarboxylate (Compound 1)

To 2.5g of 12-methoxy-5-(2-methyl-4-thiazolyl)aniline were added 100 mL of water and 50 mL of concentrated HCl and the resultant mixture was stirred −5° C. A solution of 1 g of sodium nitrite in 10 mL of water was then added dropwise, maintaing a temperature of −5° C. After this addition, the mixture was stirred at −5° C. for 1 hour. A solution of 10 g of stannous chloride in 20 mL of concentrated HCl was then added quickly to the mixture which was then stirred for 1 hour, neutralized with sodium hydroxide and extracted with dichloromethane. Evaporation of the dichloromethane gave 1.5 g of the intermediate 2-methoxy-5-(2-methyl-4-thiazolyl)-phenylhydrazine as an oil which was dissolved in 100 mL of toluene.

To the intermediate/toluene solution was added 1 g of pyridine followed by the dropwise addition of 5 mL of 1-methylethyl chloroformate solution (1M in toluene). After stirring for 1 hour, the mixture was washed with water and evaporated to a solid. The solid was washed well with hexane leaving 1.5 g of 1-methylethyl 2-[2-methoxy-5-(2-methyl-4-thiazolyl)phenyl]hydrazinecarboxylate (mp 127°–130° C.).

EXAMPLE 2

Preparation of 1-methylethyl [2-methoxy-5-(2-methyl-4-thiazolyl)phenyl] diazenecarboxylate (Compound 7)

To 1.5 g of the 1-methylethyl 2-[2-methoxy-5-(2-methyl-4-thiazolyl)phenyl]hydrazinecarboxylate of Example 1, was added 100 mL of toluene and 0.5g of palladium (10% on carbon). The mixture was vigorously stirred overnight at room temperature, then filtered and the toluene evaporated under reduced pressure. The product obtained was 1.2 g of 1-methylethyl [2-methoxy-5-(2-methyl-4thiazolyl)phenyl] diazenecarboxylate as a red oil.

The compounds summarized in Tables 1 and 2 were prepared using the procedures described above. Each of the compounds so formed is characterized by their proton NMR characteristics.

The intermediate prepared in the preparation of Compound 1 is described in Example 1 above. Compounds 2–6 were made from intermediate compounds identified below.

| Compound No. | Intermediate |
| --- | --- |
| 2 | 2-methoxy-5-(2-methyl-4-thiazolyl)phenylhydrazine |
| 3 | 2-methoxy-5-(2-pyridinyl)-phenylhydrazine |
| 4 | 2-methoxy-5-(2-thienyl)-phenylhydrazine |
| 5 | 2-methyl-5-(2-thienyl)-phenylhydrazine |
| 6 | (2-methoxy-9H-fluoren-3-yl)-hydrazine |
| 7 | (2-methoxy-5-(2-thiazolyl)-phenylhydrazine |
| 8 | 2-methoxy-5-(3-thienyl)-phenylhydrazine |

TABLE 1

$$\underset{R^1}{\underset{|}{\bigcirc}}\overset{R}{\underset{|}{-}}NHNHCO_2R^2 \quad (I)$$

| Compound No. | R | R¹ | R² | NMR DATA (CDCL$_3$)(PPM) |
|---|---|---|---|---|
| 1 | OCH$_3$ | 2-methyl-4-thiazolyl | CH(CH$_3$)$_2$ | d(6)1.2; s(3)2.2; s(3)3.9; m(1)5.0; m(4)7.0–7.6 |
| 2 | OCH$_3$ | 2-pyridinyl | CH(CH$_3$)$_2$ | d(6)1.2; s(3)3.9; m(1)5.0; m(7)7.0–9.0 |
| 3 | OCH$_3$ | 2-thienyl | CH(CH$_3$)$_2$ | d(6)1.2; s(3)3.9; m(1)5.0; m(6)7.0–7.6 |
| 4 | OCH$_3$ | 3-pyridinyl | CH(CH$_3$)$_2$ | d(6)1.2; s(3)3.9; m(1)5.0; m(7)7.0–9.0 |
| 5 | CH$_3$ | 3-pyridinyl | CH(CH$_3$)$_2$ | d(6)1.2; s(3)2.2; m(1)5.0; m(7)7.0–9.0 |
| 6 | OCH$_3$ | 9H-fluoren-3-yl | CH(CH$_3$)$_2$ | d(6)1.2; s(2)3.7; m(1)5.0; m(6)7.0–7.7 |
| 7 | CH$_3$ | 2-thiazolyl | CH(CH$_3$)$_2$ | d(6)1.2; s(3)2.2; m(1)5.0; m(6)7.0–7.6 |
| 8 | OCH$_3$ | 3-thienyl | CH(CH$_3$)$_2$ | d(6)1.2; s(3)3.9; m(1)5.0; m(6)7.0–7.6 |

TABLE 2

$$\underset{R^1}{\underset{|}{\bigcirc}}\overset{R}{\underset{|}{-}}N=N-CO_2R^2 \quad (II)$$

| Compound No. | R | R¹ | R² | NMR DATA (CDCL$_3$, PPM) |
|---|---|---|---|---|
| 9 | OCH$_3$ | 2-methyl-4-thiazolyl | CH(CH$_3$)$_2$ | d(6)1.4; s(3)2.3; m(1)5.0; m(4)7.0–7.6 |
| 10 | OCH$_3$ | 3-thienyl | CH(CH$_3$)$_2$ | d(6)1.4; 5(3)4.0; m(1)5.0; m(6)7.0–7.6 |

EXAMPLE 3

Preparation of Formulations

The remaining examples relate to the pesticidal use of the compounds of this invention. In all these examples a stock solution for the compounds was prepared at 3000 ppm by dissolving 0.3 gram of each compound to be tested in 10 ml of acetone and adding 90 ml of distilled water plus four drops of ethoxylated sorbitan monolaurate, or a simliar suitable wetting agent, to provide a stock solution for each tested compound. For each example that follows, this stock solution was used and the specificied dilutions made. All the tests discussed below, which involved treatment with compounds of this invention at concentrations of 500 and 40 ppm, were always repeated with controls, in which the active compound was not, provided, to permit a comparison upon which the percent control was calculated.

EXAMPLE 4

Mite Adulticide and Mite Ovicide/Larvicide Tests

One day before treatment, a "Figure 8" configuartion of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when all mites were removed. Plants were sprayed to run off with a 1000 ppm solution diluted from the 3000 ppm stock solution.

One day following treatment, groups of approximately 25 adult mites were transferred into the adulticide rings. Five days later these rings were examined for live mites remaining on the leaves. The percent control was estimated based on the number of mites surviving on the plants.

Nine days following treatment the ovicide/larvicide rings were examined for hatched eggs and living immature mites. The percent control was estimated based on the number of eggs hatching and immature mites surviving on the plants. When the treatment effect was to eggs, control was designated as ovicidal (O); when the treatment effect was to immatures, control was designated as larvicidal (L).

Results of the mite adulticide (MI) and ovicide/larvicidie (MIOLV) tests are presented in Table 3.

EXAMPLE 5

Nematode Test

The stock solution of 3000 ppm was diluted to 1000 ppm. For each compound, 25 ml was drenched onto 500 grams of soil infested with root knot nematode (*Meloidogyne incognita*) eggs in a pot, for a soil concentration of 50 ppm sc.

One day after treatment, two tomato seedlings were planted in each pot. Nineteen days after planting, the roots were evaluated for the presence of knots or galls, and the percent control was estimated based on the infestation levels in the plants.

The results of the nematode (NE) tests are given in Table 3.

TABLE 3

| | Percent Control | | |
|---|---|---|---|
| Compound No. | MI | MIOVL | NE |
| 1 | 100 | 100(L) | 0 |
| 2 | 100 | 70(O) | 50 |
| 3 | 98 | 90(L) | 100 |
| 4 | 98 | 0 | 0 |
| 5 | 100 | 30(O) | 0 |
| 6 | 100 | 70(O) | 0 |
| 7 | 100 | 50(O) | 0 |
| 8 | 100 | 100(O) | 70 |
| 9 | 100 | 50(O) | 0 |
| 10 | 100 | 100(O) | 100 |

What is claimed is:

1. A compound having the formula:

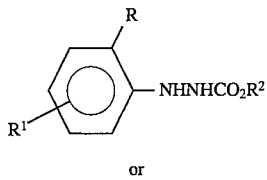

or

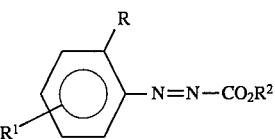

wherein R is $C_1-C_6$ alkoxy or $C_1-C_6$ alkyl; $R^1$ is fluorenyl, thienyl, pyridyl or thiazolyl, unsubstituted or substituted by one or more substituents selected from $C_1-C_4$ alkoxy, $C_1-C_4$ alkyl, $C_1-C_4$ alkylthio, halogen, $C_1-C_4$ haloalkyl and nitro; and $R^2$ is $C_1-C_6$ alkyl, $C_3-C_6$ cycloalkyl, $C_1-C_6$ haloalkyl, $C_2-C_6$ alkenyl, or $C_2-C_6$ alkoxyalkyl.

2. A compound as recited in claim 1 wherein R is $C_1-C_4$ alkoxy or $C_1-C_4$ alkyl.

3. A compound as recited in claim 2 wherein R is methoxy or methyl.

4. A compound as recited in claim 1 wherein $R^1$ is fluorenyl, thienyl, pyridyl or thiazolyl, unsubstituted or substituted by one or more $C_1-C_4$ alkyl.

5. A compound as recited in claim 4 wherein $R^1$ is 2-methyl-4-thiazolyl, 2-pyridinyl, 2-thienyl, 3-pyridinyl, or 9H-fluoren-3-yl.

6. A compound as recited in claim 1 wherein $R^2$ is $C_1-C_4$ alkyl.

7. A compound as recited in claim 6 wherein $R^2$ is 1-methylethyl.

8. A compound as recited in claim 1 wherein R is $C_1-C_4$ alkoxy or $C_1-C_4$ alkyl; $R^1$ is fluorenyl, thienyl, pyridyl or thiazolyl, unsubstituted or substituted by one or more $C_1-C_4$ alkyl; and $R^2$ is $C_1-C_4$ alkyl.

9. A compound as recited in claim 8 wherein R is methoxy or methyl; $R^1$ is 2-methyl-4-thiazolyl, 2-pyridinyl, 2-thienyl, 3-pyridinyl, or 9H-fluoren-3-yl; and $R^2$ is 1-methylethyl.

10. A compound as recited in claim 1 wherein the compound has the formula

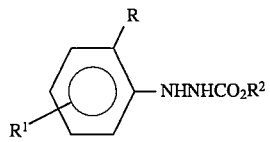

wherein R, $R^1$ and $R^2$ are as defined in claim 1.

11. A compound as recited in claim 1 wherein the compound has the formula

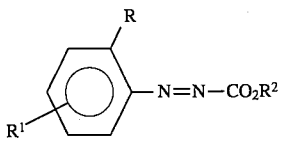

wherein R, $R^1$ and $R^2$ are as defined in claim 1.

12. An intermediate hydrazine compound of the formula

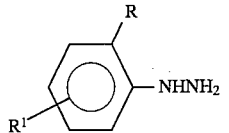

wherein R is $C_1-C_6$ alkoxy or $C_1-C_6$ alkyl; and $R^1$ is fluorenyl, thienyl, pyridyl or thiazolyl, unsubstituted or substituted by one or more substituents selected from $C_1-C_4$ alkoxy, $C_1-C_4$ alkyl, halogen, $C_1C_4$ haloalkyl and nitro.

13. An-intermediate hydrazine compound as recited in claim 12 wherein R is $C_1-C_4$ alkoxy or $C_1-C_4$ alkyl; and $R^1$ is fluorenyl, thienyl, pyridyl or thiazolyl, unsubstituted or substituted by one or more $C_1-C_4$ alkyl.

14. An intermediate hydrazine compound as recited in claim 13 wherein R is methoxy or methyl; and $R^1$ is 2-methyl-4-thiazolyl, 2-pyridinyl, 2-thienyl, 3-pyridinyl, or 9H-fluoren-3-yl.

15. A miticidal composition comprising a miticidally effective amount of a compound as recited in claim 1 and an acceptable carrier.

16. A miticidal composition comprising a miticidally effective amount of a compound as recited in claim 8 and an acceptable carrier.

17. A miticidal composition comprising a miticidally effective amount of a compound as recited in claim 9 and an acceptable carrier.

18. A method for controlling undesirable mites which comprises applying to a locus to be protected a miticidally effective amount of a compound as recited in claim 1.

19. A method for controlling undesirable mites which comprises applying to a locus to be protected a miticidally effective amount of a compound as recited in claim 8.

20. A method for controlling undesirable mites which comprises applying to a locus to be protected a miticidally effective amount of a compound as recited in claim 9.

* * * * *